United States Patent [19]

Neurath et al.

[11] Patent Number: 4,803,156

[45] Date of Patent: Feb. 7, 1989

[54] PEPTIDE-BETA-LACTAMASE CONJUGATES FOR ENZYME-LINKED IMMUNOASSAYS

[75] Inventors: Alexander R. Neurath, New York, N.Y.; Stephen B. H. Kent, Pasadena, Calif.; Nathan Strick, Far Rockaway, N.Y.

[73] Assignees: New York Blood Center, New York, N.Y.; California Institute of Technology, Pasadena, Calif.

[21] Appl. No.: 774,829

[22] Filed: Sep. 11, 1985

[51] Int. Cl.⁴ .............................................. G01N 33/53

[52] U.S. Cl. .......................................... 435/7; 435/18; 435/19

[58] Field of Search .................................... 435/7, 231

[56] References Cited

PUBLICATIONS

Yolken et al., "The Use of Beta-Lactamase in Enzyme Immunoassays for Detection of Microbial Antigens", *Journal of Immunological Methods,* 73, 109–123 (1984).

Neurath et al., "Radioimmunoassay and Enzyme-Linked Immunoassay of Antibodies . . . ", *Journal of Virological Methods,* 11, 75–86 (1984).

Borkar et al.—Chem. Abst., vol. 102 (1985) p. 198721b.

Yolken et al.—J. Clin. Microbiol., vol. 19, No. 3 (1984) pp. 356–360.

Villa-Komaroff et al.—Chem. Abst., vol. 89 (1978) p. 159988n.

Joshi et al.—Chem. Abst., vol. 91 (1979) p. 153815y.

*Primary Examiner*—Sam Rosen

*Attorney, Agent, or Firm*—Sprung Horn Kramer & Woods

[57] ABSTRACT

A reagent for an ELISA determination of an antibody, the reagent comprising a peptide covalently linked to beta-lactamase. The reagent can be used in the following method to detect antibodies in a sample which involves a. contacting the sample with protein A linked to a solid support,
b. incubating the sample-protein A linked to the solid support,
c. washing the incubated sample-protein A linked to the solid support,
d. contacting the washed sample-protein A with the reagent,
e. incubating the sample-protein A and reagent,
f. washing the incubated sample-protein A-reagent, and
g. determining the enzymatic activity of the resultant mass.

10 Claims, 3 Drawing Sheets

Pre-S protein

```
                           1                   2                   3                   4                   5                   6
         1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2

1 ayw    G H H I L G N K I Y S M G Q N L S T S N P L G F F P D H Q L D P A F R A N T A N P D W D F N P N K D T W P D A N K V G A G A
2 adyw   G H H I L G N K S Y S M G Q N L S T S N P L G F F P D H Q L D P A F R A N T N N P D W D F N P N K D T W P D A N K V G A G A
3 adw2   M G G W S S K P R K G M G T N L S V P N P L G F F P D H Q L D P A F G A N S N N P D W D F N P V K D D W P A A N Q V G V G A
4 adw    L G N K S Y S I R K G M G T N L S V P N P L G F L P D H Q L D P A F G A N S T N P D W D F N P I K D H W P A A N Q V G V G A
5 adr    M G G W S S K P R Q G M G T N L S V P N P L G F F P D H Q L D P A F G A N S N N P D W D F N P N K D Q W P E A N Q V G A G A

                               M G   N L S     N P L G F   P D H Q L D P A F   A N     N P D W D F N P   K D   W P   A N   V G   G A

         6             7                   8                   9                  10                  11                  12
         3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4

1 ayw    F G L G F T P P H G G L L G W S P Q A Q G I L Q T L P A N P P P A S T N R Q S G R Q P T P L S P P L R N T H P Q A M Q W N S
2 adyw   F G L G F T P P H G G L L G W S P Q A Q G I M Q T L P A N P P P A S T N R Q S G R Q P T P L S P P L R T T H P Q A M H W N S
3 adw2   F G P R L T P P H G G I L G W S P Q A Q G I L T T V S T I P P P A S T N R Q S G R Q P T P I S P P L R D S H P Q A M Q W N S
4 adw    F G P G L T P P H G G I L G W S P Q A Q G I L T T V S T I P P P A S T N R Q S G R Q P T P I S P P L R D S H P Q A M Q W N S
5 adr    F G P G F T P P H G G L L G W S P Q A Q G I L T T V P A A P P P A S T N R Q S G R Q P T P I S P P L R D S H P Q A M Q W N S

         F G       T P P H G G   L G W S P Q A Q G I     T         P P P A S T N R Q S G R Q P T P   S P P L R     H P Q A M   W N S

        12        13                  14                  15                  16                  17
         5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4

1 ayw    T T F H Q T L Q D P R V R G L Y F P A G G S S S G T V N P V L T T A S P L S S I F S R I G D P A L N
2 adyw   T T F H Q T L Q D P R V R G L Y F P A G G S S S G T V N P V P T T T S P I S S I F S R I G D P A L N
3 adw2   T A F H Q T L Q D P R V R G L Y L P A G G S S S G T V N P A P N I A S H I S S I S A R T G D P V T N
4 adw    T A L H Q A L Q D P R V R G L Y L P A G G S S S G T V N P A P N I A S H I S S I S A R T G D P V T I
5 adr    T T F H Q A L L D P R V R G L Y F P A G G S S S G T V N P V P T T A S P I S S I F S R T G D P A P N

         T     H Q   L   D P R V R G L Y   P A G G S S S G T V N P           S     S S I     R   G D P
```

FIG. 3

PEPTIDE-BETA-LACTAMASE CONJUGATES FOR ENZYME-LINKED IMMUNOASSAYS

BACKGROUND OF THE INVENTION

The present invention concerns reagents for an ELISA determination of antibodies. More particularly, the present invention concerns a peptide-beta-lactamase conjugate. Even more particularly, the present invention relates to an enzyme-linked immunoassay (ELISA) applicable for the screening of sera from vaccinated individuals and from individuals who have been infected with hepatitis B virus (HBV) for antibodies specific for the pre-S region of the hepatitis B virus envelope protein.

The major protein component of the hepatitis B virus(HBV) envelope (env) and of subviral hepatitis B surface antigen particles (HBsAg) is a relatively hydrophobic, cysteine-rich sequence of 226 amino acids having a molecular weight of 25 kD. The antigenicity and immunogenicity of this protein (designated as S-protein) depends on the maintenance of disulphide bonds (G. N. Vyas, K. R. Rao and A. B. Ibrahim, "Australia Antigen (Hepatitis B Antigen): A Conformational Antigen Dependent On Disulphide Bonds", *Science,* 178, 130–1301, (1972); N. Sukeno, R. Shirachi and N. Ishida, "Reduction And D.K. Reoxidation of Particle Structure And Antigenicity", *Journal Of Virology,* 9, 182–183, 1972; G. R. Dressman, F. B. Hollinger, R. M. McCombs and J. L. Melnick, "Alteration Of Hepatitis B Antigen (HBAg) Determinants By Reduction And Alkylation", *Journal of General Virology,* 19, 129–134, 1973).

The open reading frame on HBV DNA coding for S protein (P. Charnay, E. Mandart, A. Hampe, F. Fitoussi, P. Tiollais, F. Galibert, "Localization Of The Viral Genome And Nucleotide Sequence Of The Gene Coding For The Major Polypeptide Of The Hepatitis B Surface Antigen (HBsAg)", *Nucleic Acid Research,* 1, 335–346, 1979; D. L. Peterson, I. M. Roberts and G. N. Vyas, "Partial Amino Acid Sequence Of Two Major Component Polypeptides Of Hepatitis B Surface Antigen", *Proceedings Of The National Academy Of Science, U.S.A.,* 74, 1530–1534, 1977) has the capacity to code for a protein consisting of 389–400 amino acids (depending on the antigenic subtype of HBV). The DNA sequence corresponding to this reading frame and preceding the gene for S-protein (=S-gene) has been designated as the pre-S region (P. Tiollais, P. Charnay and G. N. Vyas, "Biology Of Hepatitis B Virus", *Science,* 213, 406–411, 1981).

Proteins larger than the S-protein (in its non-glycosylated (25 kD) form or glycosylated (29kD) form) have been conclusively identified in the HBV envelope and in HBsAg. Antigenic determinants specific for these proteins, but absent on S-protein, have been clearly discerned (A. Machida, S. Kishimoto, H. Ohnuma, K. Baba, Y. Ito, H. Miyamoto, G. Funatsu, K. Oda, S. Usuda, S. Togami, T. Nakamura, Y. Miyakawa and M. Mayumi, "A Polypeptide Containing 55 Amino Acid Residues Coded By The Pre-S Region Of Hepatitis B Virus-Deoxyribonucleic Acid Bears The Receptor For Polymerized Human As Well As Chimpanzee Albumins", *Gastroenterology,* 86, 910–918, 1984; A. R. Neurath, S. B. H. Kent and N. Strick, "Location And Chemical Synthesis Of A Pre-S Gene Coded Immunodominant Epitope of Hepatitis B Virus", *Science,* 224, 392–395, 1984; K. H Heermann, V. Goldmann, W. Schwartz, T. Seyffarth, H. Baumgarten and W. H. Gerlich, "Large Surface Proteins of Hepatitis B Virus Containing The Pre-S Sequence", *Journal Of Virology,* 52, 396–402, 1984).

Work with synthetic peptide analogs and with recombinant DNA containing portions of the pre-S region nucleotide sequence have established that the protein moieties of HBV (HBsAg) components with molecular weights greater than 29 kD correspond to the following sequences: (a) the "middle" protein representing the S-protein with 55 additional amino acids at the N-terminal and coded for by the pre-S region of the env gene (amino acid residues pre-S(120–174)) and (b) the "large" protein consisting of the "middle" protein with an additional 108–119 N-terminal amino acids (depending on the antigenic subtype; amino acid residues pre-S(1–119) or pre-S(12–119) (A. R. Neurath and S. B. H. Kent, "Antigenic Structure Of Human Hepatitis Viruses", *Immunochemistry Of Viruses: The Basis For Serodiagnosis And Vaccines,* 325–366, Edited by M. H. V. Van Regenmortel and A. R. Neurath, Amsterdam: Elsevier, 1985) and containing all amino acids encoded by the HBV env gene (pre-S and S regions) (A. R. Neurath, S. B. H. Kent and N. Strick, "Location And Chemical Synthesis Of A Pre-S Gene Coded Immunodominant Epitope Of Hepatitis B Virus", *Science,* 224, 392–395, 1984; A. R. Neurath, S. B. H. Kent, N. Strick, P. Taylor and C. E. Stevens, "Hepatitis B Virus Containing Pre-S Gene Encoded Domains", *Nature (London)* 315, 154–156, 1985; H. Okamoto, M. Imai, S. Usuda, B. Tanaka, K. Tachibana, S. Mishiro, A. Machida, T. Makamura, Y. Miyakama and M. Mayumi, "Hemagglutination Assay Of Polypeptide Coded By The Pre-S Region Of Hepatitis B Virus DNA With Monoclonal Antibody: Correlation Of Pre-S Polypeptide With The Receptor For Polymerized Human Serum Albumin In Serums Containing Hepatitis B Antigens", *Journal Of Immunology,* 134, 1212, 1984; M. -L. Michael, P. Pontisso, E. Sobczak, Y. Malpiece, R. E. Streeck and P. Tiollais, "Synthesis In Animal Cells of Hepatitis B Surface Antigen Particles Carrying A Receptor For Polymerized Human Serum Albumin", *Proceedings Of The National Academy Of Sciences, U.S.A.,* 81, 7708–7712, 1984; D. T. Wong, N. Nath and J. J. Sninsky, "Identification of Hepatitis B Virus Polypeptides Encoded By The Entire Pre-S Open Reading Frame", *Journal Of Virology,* 55, 223–231, 1985; D. H. Persing, H. E. Varmus and D. Ganem, "A Frameshift Mutation In The Pre-S Region Of The Human Hepatitis B Virus Genome Allows Production Of Surface Antigen Particles But Eliminates Binding To Polymerized Albumin", *Proceedings Of The National Academy Of Sciences, U.S.A.,* 82, 3440–3444, 1985; W. Stibbe and W. H. Gerlich, *Virology,* 123, 436, 1982; A. Machida, S. Kishimoto, H. Ohnuma, H. Miyamoto, K. Baba, K Oda, T. Nakamura, Y. Miyakawa and M. Mayumi, *Gastroenterology,* 85, 268 (1983)).

The pre-S sequences of the middle and large HBV env protein have the following properties distinct from S-protein: (1) a high proportion of charged amino acid residues and high hydrophilicity; (2) absence of cysteine residues; and (3) the highest HBV subtype-dependent amino acid sequence variability among HBV DNA gene products and minimal homology with pre-S sequences corresponding to nonhuman hepadnaviruses. These properties indicate that the pre-S sequences: (1) are exposed on the surface of HBV (HBsAg); (2) may determine the host range of HBV, in accordance with their involvement in attachment of the virus to hepatocytes; (3) have a disulphide-bond-independent antigenicity and immunogenicity confirmed experimentally (A. R. Neurath, S. B. H. Kent, N. Strick, "Location And Chemical Synthesis Of A Pre-S Gene Coded Immunodominant Epitope Of Hepatitis B Virus", *Science,* 224, 392–395, 1984); and (4) are recognized by the host's immune system (A. R. Neurath, S. B. H. Kent, N. Strick, "Location And Chemical Synthesis Of A Pre-S Gene Coded Immunodominant Epitope of Hepatitis B Virus", *Science,* 224, 392–395, 1984). Antigenic determinants located on pre-S sequences are more immunogenic than S-protein determinants located on the same HBsAg particle (D. R. Milich, G. B. Thornton, A. R. Neurath, S. B. H. Kent, M. -L. Michael, P. Tiollais and F. V. Chisari, "Enhanced Immunogenicity Of The Pre-S Region Of Hepatitis B Surface Antigen", *Science,* 228, 1195–1199, 1985).

The presence of pre-S sequences enhances the immune response to S-protein and circumvents the immunologic non-responsiveness to S-protein in non-responder mouse strains (Milich et al., 1985, supra; P. Coursaget, J. L. Barnes, J. P. Chiron and P. Adamowicz, "Hepatitis B Vaccines With And Without Polymerized Albumin Receptors", *Lancet,* 1, 1152–1153, 1985).

Antibodies with anti-pre-S specificity are virus-neutralizing. Accordingly, an immune response to pre-S sequences may play an important role in protection against HBV infection. Therefore, it is important to determine whether or not humans vaccinated against hepatitis B develop antibodies to pre-S-specific determinants. However, sufficiently sensitive assays for such antibodies have not heretofore been available.

HBV vaccines consisting of HBsAg prepared from serum (M. R. Hilleman, E. B. Buynak, W. J. McAleer, A. A. McLean, P. J. Provost and A. A. Tytell, *Viral Hepatitis,* W. Szmuness, H. J. Alter and J. E. Maynard, eds., The Franklin Institute Press, Philadelphia, 385, 1982) or by recombinant DNA techniques (W. J. McAleer, E. B. Buynak, R. Z. Maigetter, D. E. Wampler, W. J. Miller and M. R. Hilleman, *Nature (London),* 307, 178, 1984) which contain only the S-protein (A. R. Neurath, S. B. H. Kent, N. Strick, P. Taylor and C. E. Stevens, *Nature (London),* 315, 154, 1985) have good efficacy (C. E. Stevens, P. E. Taylor, M. J. Tong, P. T. Toy and G. N. Vyas, "Viral Hepatitis And Liver Disease", G. N. Vyas, J. L. Dienstag and J. H. Hoofnagle, eds., Grune & Stratton, Orlando, Fla., p. 275, 1984) except when administered to immunocompromised recipients (C. E. Stevens, H. J. Alter, P. E. Taylor, E. A. Zang, E. J. Harley and W. Szmuness, *N. Eng.. J. Med.,* 311, 496, 1984; J. Desmyter and J. Colaert, *Viral Hepatitis And Liver Disease,* G. N. Vyas, J. L. Dienstag and J. H. Hoofnagle, eds., Grune & Stratton, Orlando, Fla., p. 709, 1984). Serum-derived HBsAg vaccines, not submitted to treatments known to destroy the pre-S gene coded portions of the HBV env proteins (A. R. Neurath, S. B. H. Strick, P. Taylor and C. E. Stevens, 1985, supra) appeared to have a better efficacy in immunocompromised individuals than did the vaccine containing S-protein only (J. Desmyter and J. Colaert, 1984, supra; J. Desmyter, J. Colaert, G. DeGroote, M. Reynders, E. E. Reerink-Brongers, P. N. Lelie, P. J. Dees and H. W. Reesink, *Lancet,* 2, 1323, 1983).

The following findings suggest the possibility that such differences may be explained by the absence of presence of pre-S gene coded sequences in the vaccines: (1) humans recovering from hepatitis B have antibodies to pre-S gene coded determinants on the HBV middle and large env proteins (A. R. Neurath, S. B. H. Kent, N. Strick, P. Taylor and C. E. Stevens, 1985, supra); (2) such antibodies specifically interfere with the attachment of HBV to hepatocytes (A. R. Neurath, S. B. H. Kent, N. Strick, P. Taylor and C. E. Stevens, 1985, supra); (3) at least some of these antibodies are virus-neutralizing; (4) the pre-S gene coded antigenic determinants are more immunogenic than S-protein determinants located on the same HBsAg particle ( D. R. Milich, G. B. Thornton, A. R. Neurath, S. B. H. Kent, M. -L. Michel, P. Tiollais and F. V. Chisari, *Science,* 228, 1195, 1985); (5) immunologic nonresponsiveness to S-protein can be overcome by immunization with pre-S gene coded sequences of the HBV env middle protein (D. R. Milich, G. B. Thornton, A. R. Neurath, S. B. H. Kent, M.-L. Michel, P. Tiollais and F. V. Chisari, 1985, supra); and (6) the presence of pre-S sequences enhances the immune response to S-protein (P. Coursaget, J. L. Barres, J. P. Chiron and P. Adamovicz, *Lancet,* 1, 1152, 1985), (D. R. Milich, G. B. Thornton, A. R. Neurath, S. B. H. Kent, M. -L. Michel, P. Tiollais and F. V. Chisari, 1985, supra).

In order to better understand the protective responses elicited by hepatitis B vaccines, it would be desirable to test: (1) hepatitis B vaccines for the presence and level of pre-S sequences and (2) recipients of the vaccines for the corresponding humoral and cell-mediated immune responses. Another problem of high significance and medical importance is the detection in human sera of antibodies to the lymphotropic virus type III (HTLV III/LAV). These antibodies serve as a marker for past or present infection with HTLV III/LAV. They can be a tool for screening of blood donors to assure the safety of blood and blood products. Presently available methods for detection of these antibodies are not sufficiently specific and require additional confirmatory tests.

The enzyme-linked immunoassay technique is increasingly popular because it is very sensitive and does not require specialized equipment, as do immunofluorescence and radioimmunoassay. The method depends on conjugation of an enzyme to either an antigen (Ag) or an antibody (Ab) and use of the enzyme activity as a quantitative label. Many variations of the method can be constructed, depending on the nature of the enzyme employed and the Ag-Ab system to be measured. A widely employed variant is the enzyme-linked immunosorbent assay (ELISA), which can be used to measure either Ag or Ab. To measure Ab, the known Ag is fixed to a solid phase (e.g., plastic cup or microplate), incubated with test serum dilutions, washed and then incubated with anti-immunoglobulin labeled with an enzyme (e.g., horseradish peroxidase). Enzyme activity is measured by adding the specific substrate: the color reaction is estimated colorimetrically. The enzyme activity is a direct function of the amount of antibody bound.

To measure Ag, a known specific Ab is fixed to the solid phase, the test material containing Ag is added and washed, and a second enzyme-labeled Ab is added. This test requires that the Ag have at least two determinants. After washing, substrate is added and enzyme activity is estimated colorimetrically and related to Ag concentration.

U.S. Pat. Nos. b 3,654,090 and 4,343,896, describe methods for determining antigens and antibodies using antigens or antibodies covalently linked to enzymes.

Enzymes described therein include peroxidase, beta-glucuronidase, beta-D-glucosidase, beta-D-galactosidase, urease, glucose oxidase+peroxidase and galactose oxidase+peroxidase.

Enzymes considered to be suitable for ELISA are described in U.S. Pat. No. 3,839,153. Such enzymes listed include catalase, peroxidase, beta-glucuronidase, beta-D-glucosidase, beta-D-galactosidase, urease, glucose oxidase, galactose oxidase and alkaline phosphatase.

An enzymatic immunological method for the determination of antigens and antibodies is described in U.S. Pat. No. 4,106,043. The preferred enzyme in U.S. Pat. No. 4,106,043 is horseradish peroxidase. Other listed enzymes include catalase, peroxidase, urease, glucose oxidase and alkaline phosphatase.

U.S. Pat, Nos. 4,169,012 and 4,228,240 are directed to a stabilized peroxidase reagent for enzyme immunoassay, i.e., peroxidase and a metal ion, e.g., Mg, Ca, Sc, Ti, V, Cr, Mn, Fe, Co, Ni, Co, Zn, Ga and Al.

U.S. Pat. No. 3,850,752 lists the following enzymes for coupling to a hapten, protein or antibody: catalase, peroxidase, beta-glucuronidase, beta-D-glucosidase, beta-D-galactosidase, urease, glucoseoxidase and galactose-oxidase.

U.S Pat. No 3,879,262 concerns the detection and determination of haptens. The following enzymes are describe for use therein: catalases, peroxidases, glucuronidases, glucosidases, galactosidases, urease and oxidoreductases (glucose oxidase and galactose oxidase).

Although a number of different hepatitis B vaccines have good efficacy in immunocompetent recipients, there are obvious differences between distinct vaccines (Desmyter and Colaert, 1984 supra). The variety of hepatitis B vaccines is expected to increase in the near future. Therefore, the need for studies comparing their immunogenicities using standardized techniques will also increase. These should include methods for detection and quantitation of all HBV-specific proteins in the vaccines and the quantitation of specific antibodies elicited in vaccine recipients.

SUMMARY OF THE INVENTION

It is an object of this invention to provide a reagent for an ELISA determination of an antibody.

It is another object of the present invention to provide a reagent for the determination of antibodies specific for the pre-S region of the hepatitis B virus envelope protein.

Another object of the present invention resides in the determination of antibodies specific for the HTLV III/LAV virus.

The above objects and other objects are realized by the present invention wherein a reagent for an ELISA determination of antibody comprises a peptide covalently linked to beta-lactamase.

The present invention further concerns a reagent for an ELISA determination of antibodies specific for the pre-S region of the hepatitis B virus envelope protein, wherein the reagent includes beta-lactamase covalently linked to a synthetic peptide having an amino acid sequence corresponding to a sequence of amino acids in the pre-S region of the hepatitis B virus envelope protein.

The present invention also relates to a reagent for an ELISA determination of antibodies specific for HTLV III/LAV virus.

The present invention also concerns a method for detecting a given antibody in a sample comprising a. contacting the sample with protein A on a solid support, e.g., polystyrene beads,
b. incubating the resultant mass from step a, (protein A-antibody complex),
c. washing the resultant mass from step b,
d. contacting the washed mass from step c with a peptide-beta-lactamase conjugate,
e. incubating the resultant mass from step d,
f. washing the resultant mass from step e, and
g. determining the enzymatic activity of the resultant mass from step f.

DEFINITIONS

DEFINITIONS
Amino Acid Code Words (as appearing in FIG. 3)

| | | |
|---|---|---|
| D | Asp | aspartic acid |
| N | Asn | asparagine |
| T | Thr | threonine |
| S | Ser | serine |
| E | Glu | glutamic acid |
| Q | Gln | glutamine |
| P | Pro | proline |
| G | Gly | glycine |
| A | Ala | alanine |
| C | Cys | cysteine |
| V | Val | valine |
| M | Met | methionine |
| I | Ile | isoleucine |
| L | Leu | leucine |
| Y | Tyr | tyrosine |
| F | Phe | phenylalanine |
| W | Trp | tryptophane |
| K | Lys | lysine |
| H | His | histidine |
| R | Arg | arginine |
| HBV | | hepatitis B virus |
| HBsAg | | hepatitis B surface antigen |
| DNA | | deoxyribonucleic acid |

DESCRIPTION OF THE DRAWINGS

FIG. 3 shows amino acid sequences of the translational products of the pre-S gene region deduced from sequences of HBV DNA. The sequences are presented in one-letter amino acid code words (such code words are defined in the Definitions herein). Sequences for five distinct HBV subtypes are presented. The 6th bottom line shows amino acid residues common to all five subtypes.

DETAILED DESCRIPTION OF THE INVENTION

Figure 1:
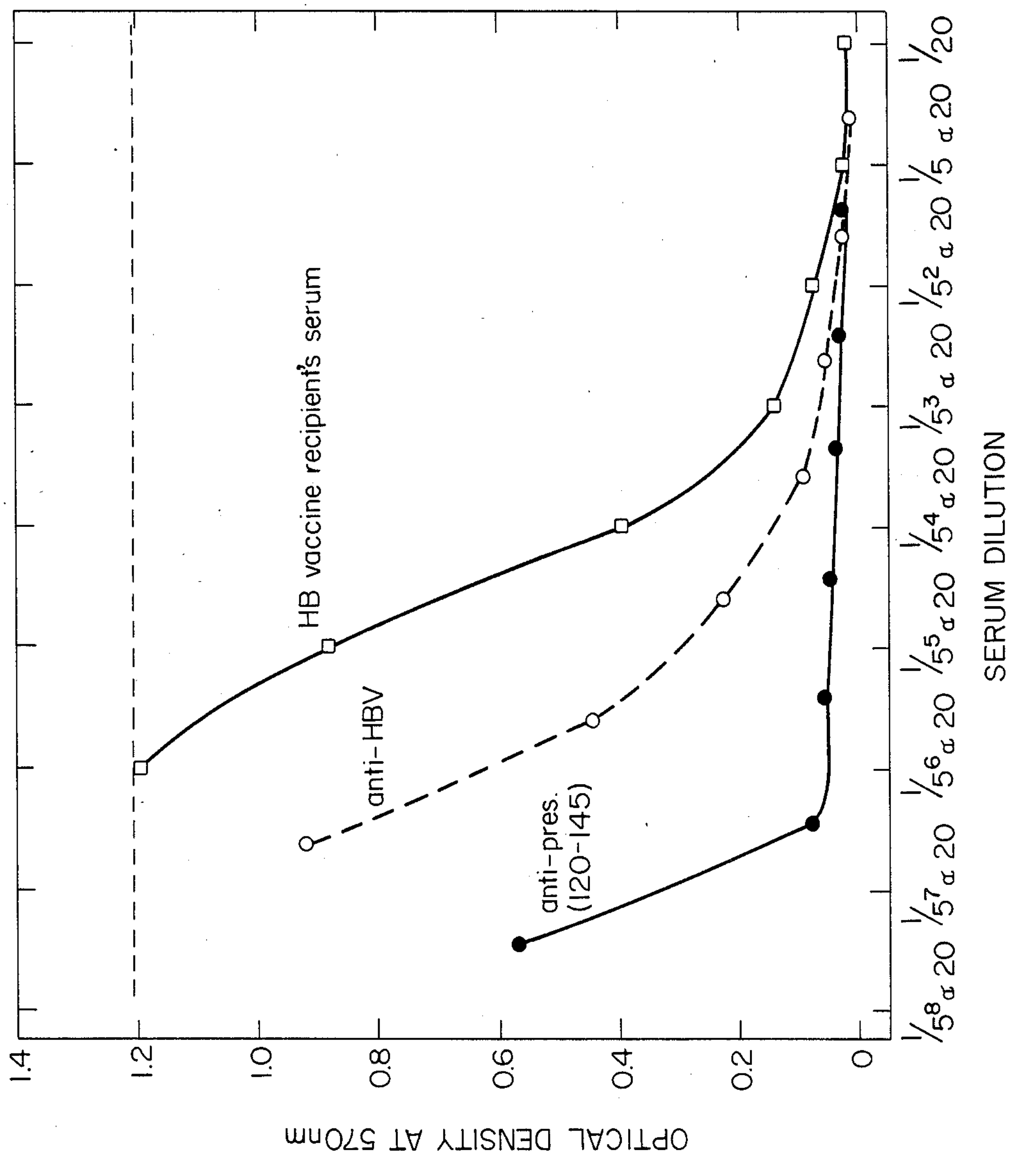
FIG. 1 depicts a graph of optical density (ordinate) vs. serum dilution (abscissa) for results of ELISA tests with serial dilutions of rabbit antisera to HBV (A. R. Neurath, C. Trepo, M. Chen and A. M. Prince, "Identification of Additional Antigenic Sites On Dane Particles and Tubular Forms of Hepatitis B Surface Antigen", *Journal of General Virology*, 30, 277–285, 1976; and to the synthetic peptide pre-S(120–145) (Neurath et al., 1984, supra); and of a serum from a recipient of a hepatitis B vaccine (V. J. McAuliffe, R. H. Purcell, J. L. Gerin and F. J. Tyeryar, "Current Status Of The NIAID Hepatitis B Vaccines", *Viral Hepatitis*, pp. 425–435. Edited by W. Szmuness, H. J. Alter, J. E. Maynard. Philadelphia: Franklin Institute Press, 1982.) are plotted. The enzyme-labelled antigen was pre-S(120–145)-beta-lactamase. Dashed horizontal line indicates optical density ($OD_{570}$) corresponding to substrate. Note that decreased pre-S(120–145)-beta lactamase binding to magnetic protein A at higher serum dilutions results in higher $OD_{570}$ readings, indicating a decreasing decolorization of the substrate.

Antibodies recognizing preselected regions of a protein can be generated by immunization with appropriate synthetic peptides. The application of such antibodies, having predetermined specificity, in biology and medicine is becoming increasingly attractive (R. A. Lerner, "Tapping The Immunological Repertorie To Produce Antibodies of Predetermined Specificity", *Nature (London),* 299, 592–596, 1982). Synthetic peptide analogues also offer the opportunty to serve as reagents for discerning antibodies of predetermined specificity among the repertoire of antibodies produced by immunization with complex proteins, viruses and their subunits. This may be especially advantageous in the search for antibodies specifically recognizing biologically important epitopes.

Domains encoded by the pre-S region of the HBV env gene play a significant role in the life cycle of HBV (A. R. Neurath, S. B. H. Kent, N. Strick and C. E. Stevens, "Hepatitis B Virus Contains Pre-S Gene Encoded Domains", *Nature (London),* 315, 154–156, (1985). Therefore, it has become important to detect antibodies recognizing these domains in sera of humans who had been infected with HBV or who were immunized with hepatitis B vaccines. Earlier studies (A. R. Neurath, S. B. H. Kent, N. Strick, "Location And Chemical Synthesis Of A Pre-S Gene Coded Immunodominant Epitope Of Hepatitis B Virus", *Science,* 224, 392–395, 1984; A. R. Neurath, S. B. H. Kent, N. Strick, P. Taylor and C. E. Stevens, "Hepatitis B Virus Contains Pre-S Gene Encoded Domains", *Nature (London),* 315, 154–156, 1985) established that anti-HBV sera recognize at high dilutions a synthetic peptide pre-S(120–145) corresponding to the 26 N-terminal amino acids (encoded by the pre-S gene) of the HBV middle protein. Therefore, it is believed that this peptide could represent the basis for the design of an assay more sensitive than the tests used heretofore. Applicants herein indeed developed such an assay using a pre-S peptide-beta-lactamase conjugate, e.g., a pre-S(120–145) beta-lactamase conjugate. This particular conjugate lead to an assay 50 to 100 times more sensitive than the preceding tests. Without wishing to be bound by any particular theory of operability, it is believed that the enhanced sensitivity afforded by the conjugates of this invention are the result of a glutaraldehyde induced polymerization between the peptide and beta-lactamase which leads to products preferentially recognized by antibodies elicited by HBV (HBsAg) containing pre-S sequences.

Applicants have developed an assay for antibodies specifically recognizing the HBV large protein. This assay is based on the synthetic peptide pre-S(12–32) linked to beta-lactamase (a pre-S(12–32)-beta-lactamase conjugate).

Since the content of the HBV large protein in HBsAg is usually much lower than the content of the middle protein (Heermann et al., 1984, supra; A. R. Neurath, Nathan Strick, P. Taylor and S. B. H. Kent, 1985, supra), the dilution endpoints of sera from vaccinated persons were by two orders of magnitude lower in this assay as compared to endpoints in ELISA utilizing pre-S(120–145)-beta lactamase. (see FIG. 1 and FIG. 2). This assay is (1) useful for studying the antibody repertoire in sera of persons who have been infected with HBV or who were vaccinated against hepatitis B virus, and (2) potentially important for immunogencity studies on hepatitis B vaccines.

The use of synthetic peptide-beta-lactamase conjugates in combination with magnetic protein A offers a good opportunity for the development of screening assays for detection of anti-viral antibodies in general. The availability of protein A expressed in E. coli (Repligen, Cambridge, MA) makes such assays economically feasible. Such assays should permit the detection of antibodies specifically reacting with defined functional domains of a virus if sequences corresponding to these domains are determined.

The physical structure and proposed genetic organization of the HBV genome are described by P. Tiollais, P. Charnay and G. N. Vyas, *Science,* 213, 1981 at pp. 408–409.

There are two DNA strands, namely the long (L) strand and the short (S) strand. The L strand transcipt has four open reading frame regions which are termed (S+pre-S), C, P and X.

The open reading frame region (S+pre-S) corresponds to the envelope (env) gene of HBV DNA and codes for a family of proteins found in the HBV envelope and in virus related particles.

A schematic representation of the potential translation products of the env gene(s) of HBV DNA is as follows:

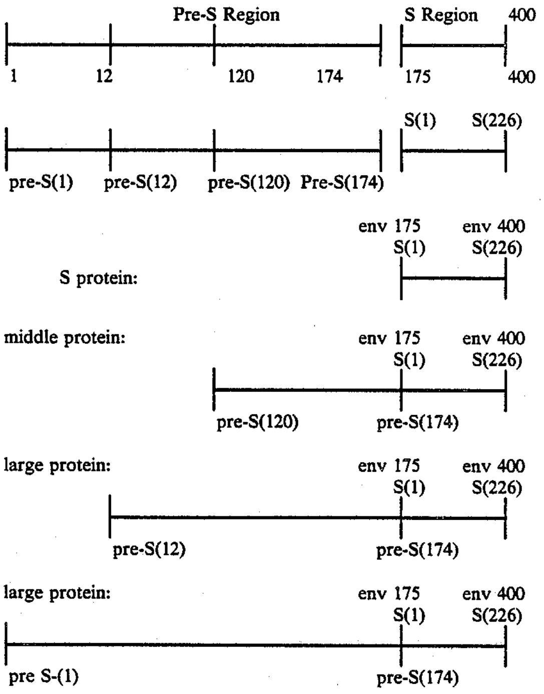

The numbers in the above schematic refers to amino acids (AA). A translation initiation site at Met 1 exists for the adw$_2$ and adr subtypes only. The first amino acid for the other subtypes correspond to position pre-S 12.

Hereinafter, amino acid sequences corresponding to the pre-S region (env 1 to 174) are designated with the prefix "pre-S" and amino acid sequences corresponding to the S region (env 175 to 400) are designated by the prefix "S". In the env gene product representation, the S region spans amino acids 175 to 400 as compared to amino acids 1 to 226 in the "S region only" representation.

In the above schematic, the pre-S region is defined by amino acid sequence positions pre-S 1 to amino acid sequence position pre-S 174. The S region is defined by sequence positions S 1 (amino acid 175 of the open reading frame and adjacent to pre-S 174) to sequence position S 226 (amino acid 400 of the open reading frame). The S-gene product (S-protein) consists of this 226 amino acid sequence.

Non-limiting pre-S peptides for linking to beta-lactamase according to the present invention include the following:

(1) pre-S(12-32), wherein the sequence is (see FIG. 3) MGTNLSVPNPLGFFPDHQLDP for subtype adw$_2$;

(2) pre-S(120-145), wherein the sequence is (see FIG. 3) MQWNSTAFHQTLQDPRVRGLYLPAGG for subtype adw$_2$;

(3) pre-S(32-53), wherein the sequence is (see FIG. 3) PAFGANSNNPDWDFNPVKDDWP for subtype adw$_2$;

(4) pre-S(117-134), wherein the sequence is (see FIG. 3) PQAMQWNSTAFHQTLQDP for subtype adw$_2$;

(5) pre-S(94-117), wherein the sequence is (see FIG. 3) PASTNRQSGRQPTPISPPLRDSHP for subtype adw$_2$;

(6) pre-S(153-171), wherein the sequence is (see FIG. 3) PAPNIASHISSISARTGDP for subtype adw$_2$;

(7) pre-S(1-21), wherein the sequence is (see FIG. 3) MGGWSSKPRKGMGTNLSVPNP for subtype adw$_2$;

(8) pre-S(57-73), wherein the sequence is (see FIG. 3) QVGVGAFGPRLTPPHGG for subtype adw$_2$;

(9) pre-S(1-11), a. for adw$_2$, wherein the sequence is (see FIG. 3) MGGWSSKPRKG b. for adr, wherein the sequence is (see FIG. 3) MGGWSSKPRQG.

Particularly preferred sequences for binding to beta-lactamase are pre-S(12-32) and pre-S(120-145).

The tests design described herein may contribute to the solution of recent problems associated with the diagnosis and prevention of the acquired immunodeficiency syndrome (AIDS). The specificity of antibody detection can be assured by using for ELISA appropriate synthetic peptides conjugated with beta-lactamase in analogy with methods for detection of anti-pre-S-specific antibodies described above.

These synthetic peptide correspond to N-terminal and C-terminal portions of the processed and cleaved env proteins of HTLV III/LAV, for example:

NH$_2$—T E K L W V T V Y Y G V P V W K E A T T T L F C — COOH
(N-terminal) ;

NH$_2$—C R A I R H I P R R I R R Q G L E R I L L — COOH
(C-terminal)

NH$_2$—R A V G I G A L F L G F L G A A G S T M G A R S M—COOH
(N-terminal) ; and NH$_2$—P G G G D M R D N W R S E L Y K Y K V V K I E P L G V A P T K A K—COOH
(C-terminal) .

The present invention can be employed as a diagnostic tool to determine the presence of specific antibodies to specific antigens by employing peptides which mimic the natural antigens. These peptides can be conjugated with beta-lactamase. Thus, for example, the following peptide which mimic the antigenic determinant of natural hepatitis B S-protein could be used in conjunction with the detection of antibodies to the S-protein.

| | | | | | | | | | | |
|---|---|---|---|---|---|---|---|---|---|---|
| 135 | 136 | 137 | 138 | 139 | 140 | 141 | 142 | 143 | 144 | 145 |
| Pro | Ser | Cys | Cys | Cys | Thr | Lys | Pro | Thr or Ser | Asp | Gly |
| 146 | 147 | 148 | 149 | 150 | 151 | 152 | 153 | 154 | 155 | |
| Asn | Cys | Thr | Cys | Ile | Pro | Ile | Pro | Ser | Ser | |

Other peptides mimicking the antigenic determinant of HBsAg (S region) include the following:

Peptide 1 (I)

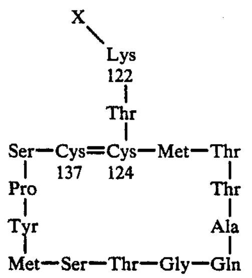

Peptide 2 contains 5 additional amino acid residues:

Ser—Thr—Gly—Pro—Ser—X,
117 121

G. R. Dreesman, Y. Sanchex, I. Ionescu-Matiu, J. T. Sparrow, H. R. Six, D. L. Peterson, F. B. Hollinger and J. L. Melnick, "Antibody to Hepatitis B Surface Antigen After A Single Inoculation of Uncoupled Synthetic HBsAg Peptides", *Nature*, 295, 158-160, 1982; and (2) the following peptides:

| POSITION | SEQUENCE |
|---|---|
| 48–81 | Cys—Leu—Gly—Gln—Asn—Ser—Gln—Ser—Pro—Thr—Ser—Asn—His—Ser—Pro—Thr—Ser—Cys—Pro—Pro—Thr—Cys—Pro—Gly—Tyr—Arg—Trp—Met—Cys—Leu—Arg—Arg—Phe—Ile |
| 2–16 | Glu—Asn—Ile—Thr—Ser—Gly—Phe—Leu—Gly—Pro—Leu—Leu—Val—Leu—Gln—Cys |
| 22–35 | Leu—Thr—Arg—Ile—Leu—Thr—Ile—Pro—Gln—Ser—Leu—Asp—Ser—Trp—Cys |
| 38–52 | Ser—Leu—Asn—Phe—Leu—Gly—Gly—Thr—Thr—Val—Cys—Leu—Gly—Gln—Asn |
| 47–52 | Val—Cys—Leu—Gly—Gln—Asn |
| 95–109 | Leu—Val—Leu—Leu—Asp—Tyr—Gln—Gly—Met—Leu—Pro—Val—Cys—Pro—Leu |
| 104–109 | Leu—Pro—Val—Cys—Pro—Leu |

R. A. Lerner, N. Green, H. Alexander, F. -T. Liu, J. G. Sutcliffe and T. M. Shinnick, "Chemically Synthesized Peptides Predicted From the Nucleotide Sequence of the Hepatitis B Virus Genome Elicit Antibodies Reactive With the Native Envelope Protein Of Dane Particles", *Proc. Natl. Acad. Sci. USA,* 78, 6, 3403–3407, 1981.

A peptide containing an amino acid sequence mimicking the antigenic determinant of coliphage MS-2 antigen is as follows:

| | | | | | | | | |
|---|---|---|---|---|---|---|---|---|
| 89 | 90 | 91 | 92 | 93 | 94 | 95 | 96 | 97 |
| Glu | Leu | Thr | Ile | Pro | Ile | Phe | Ala | Thr |
| 99 | 99 | 100 | 101 | 102 | 103 | 104 | 105 | |
| Asn | Ser | Asp | Cys | Glu | Leu | Ile | Val | |
| 106 | 107 | 108 | | | | | | |
| Lys | Ala | Met, | | | | | | |

R. Arnon, M. Sela, M. Parant and L. Chedid, "Antiviral Response Elicited by A Completely Synthetic Antigen With Built-in Adjuvanticity", *Proc. Natl. Acad. Sci USA,* 77, 11, 6769–6772, 1980.

A peptide containing an amino acid sequence mimicking the antigenic determinant of human leukocyte interferon antigen is as follows:

111
Leu—Met—Asn—Ala—Asp—Ser—Ile—Leu—Ala—Val—Lys—

124 125
—Lys—Tyr—Phe—Arg—Arg—Ile—Thr—Leu—Tyr—Leu—

138 139
—Thr—Glu—Lys—Tyr—Ser—Pro—Cys—Ala—Trp—Glu—

152
—Val—Val—Arg—Ala—Glu—Ile—Met—Arg—Ser—Leu—

153
—Ser—Leu—Ser—Thr—Asn—Leu—Gln—Glu—Arg—

166
—Leu—Arg—Arg—Lys—Glu

H. Arnheiter, R. M. Thomas, T. Leist, M. Fountlakis, and B. Gutte, "Physicochemical and Antigenic Properties of Synthetic Fragments of Human Leukocyte Interferon", *Nature,* 294, 19, 1981.

A peptide containing an amino acid sequence mimicking the antigenic determinant of human fibroblast interferon is as follows:

| | | | | | | |
|---|---|---|---|---|---|---|
| Met | Ser | Tyr | Asn | Leu | Leu | Gly |
| Phe | Leu | Gln | Arg | Ser | Ser, | |

F. Shimizu, Y. Ohmoto and K. Imagawa, "Production of Anti-IFN-beta Sera With Chemically Synthetic IFN-beta Fragment (1–13)", *Biochem and Biophys. Res. Comm.,* 103, 1149–1156, 1981.

A peptide containing an amino acid sequence mimicking the antigenic determinant of retrovirus R antigen is as follows:

Leu-Thr-Gln-Gln-Phe-His-Gln-Leu-Lys-Pro Ile-Glu-Cys-Glu-Pro,

J. G. Sutcliffe, T. M. Shinnick, N. Green, F. -T. Liu, H. L. Niman and R. A. Lerner, "Chemical Synthesis of A Polypeptide Predicted From Nucleotide Sequence Allows Detection Of A New Retroviral Gene Product", *Nature,* 287, 1980.

A peptide containing an amino acid sequence mimicking the antigenic determinant of avian sarcoma virus antigen is as follows:

Glu-Asp-Asn-Glu-Tyr-Thr-Ala-Arg-Gln-Gly,

T. W. Wong and Alan R. Goldberg, "Synthetic Peptide Fragment Of src Gene Product Inhibits the src Protein Kinase and Cross Reacts Immunologically With Avian onc Kinases and Cellular Phosphoproteins", *Proc. Natl. Acad. USA,* 78, 12, 7412–7416, 1981.

Peptides containing an amino acid sequence mimicking the antigenic determinant of foot-and-mouth disease virus antigen are as follows:

141
Val Pro Asn Leu Arg Gly Asp Leu Gly Val

160
Leu Ala Gly Lys Val Ala Arg Thr Leu Pro and

201
His Lys Gln Lys Ile Val Ala Pro Val Lys Gln
Thr Leu,

J. L. Bittle, R. A. Houghten, H. Alexander, T. M. Shinnick, J. G. Sutcliffe, R. A. Lerner, D. J. Rowlands and F. Brown, "Protection Against Foot-And-Mouth Disease By Immunization With A Chemically Synthesized Peptide Predicted From the Viral Nucleotide Sequence", *Nature,* 298, 30–33, 1982.

A peptide containing an amino acid sequence mimicking the antigenic determinant of hemagglutinin X-31 (H3N2) influenza virus antigen is as follows:

123 125 130
Glu—Gly—Phe—Thr—Trp—Thr—Gly—Val—Thr—Gln—Asn—

-continued 135 140
—Gly—Gly—Ser—Asp—Ala—Cys—Lys—Arg—Gly—Pro—

145 150 151
—Gly—Ser—Gly—Phe—Phe—Ser—Arg—Leu,

D. C. Jackson, J. M. Murray, D. O. White, C. N. Fagan and G. W. Tregear, "Antigenic Activity of a Synthetic Peptide Comprising the 'Loop' Region of Influenza Virus Hemagglutinin", *Virology,* 120, 273–276, 1982.

A peptide containing an amino acid sequence mimicking the antigenic determinant of hemagglutinin of type A H3N2 influenza virus antigen was synthesized by G. M. Muller, M. Shapira and R. Arnon, "Anti-influenza Response Achieved by Immunization With A Synthetic Conjugate", *Proc. Natl. Acad. Sci. USA,* 79, 569–573, 1982. The peptide corresponds to the sequence serine-91 to leucine-108 of the amino acid chain of the virus.

A peptide containing an amino acid sequence mimicking the antigenic determinant of polyoma virus medium size tumor antigen is Lys-Arg-Ser-Ars-His-Phe, G. Walter, M. A. Hutchinson, T. Hunter and W. Eckhart, "Purification of Polyoma Virus Medium-Size Tumor Antigen by Immunoaffinity Chromatography", *Proc. Natl. Acad. Sci USA,* 79, 4025–4029, 1982.

A peptide containing an amino acid sequence mimicking the antigenic determinant of poliovirus replicase antigen is as follows:

Tyr—Ser—Thr—Leu—Tyr—Arg—
450

—Arg—Trp—Leu—Asp—Ser—Phe
461,

M. H. Baron and D. Baltimore, "Antibodies Against a Synthetic Peptide of the Poliovirus Replicase Protein: Reaction with Native, Virus-Encoded Proteins and Inhibition of Virus-Specific Polymerase Activities In Vitro". *Jour. Virology,* 43, 3969–3978, 1982.

Peptides containing an amino acid sequence mimicking the antigenic determinant of simian virus 40 large tumor antigen are as follows:

Met-Asp-Lys-Val-Leu-Asn-Arg and

Lys-Pro-Pro-Thr-Pro-Pro-Pro-Glu-Pro-Glu-Thr,

G. Walter, K. H. Scheidtmann, A. Carbone, A. P. Laudano and R. F. Doolittle, "Antibodies Specific for the Carboxy- And Amino- Terminal Regions of Simian Virus 40 Large Tumor Antigen", *Proc. Natl. Acad. Sci USA,* 77, 9, 5179–5200, 1980.

A peptide containing an amino acid sequence mimicking the antigenic determinant of influenza virus strain 3QB antigen is Ile/ Val/ Asx$_2$ Thrl Ser$_2$ Glx$_2$ Pro$_1$ Gly$_3$ Ala$_1$ Leu$_1$ Lys$_1$, A. Aitken and C. Hannoun, "Purification of Hemagglutinin and Neuraminidase from Influenza Virus Strain 3QB and Isolation of a Peptide From an Antigenic Region of Hemagluttinin", *Eur. J. Biochem,* 107, 51–56, 1980.

Peptides containing an amino acid sequence mimicking the antigenic determinant of diptheria antigen are given as follows:

Natural DT Loop

—Cys—Ala—Gly—Asn—Arg—Val—Arg—Arg—Ser—Val—
186 190 195

-continued

—Gly—Ser—Ser—Leu—Lys—Cys—
201

| Synthetic Peptide | |
|---|---|
| Tetradecapeptide | Gly(188)—Cys—(201) |
| Hexadecapeptide | Cys(186)—Cys—(201) |
| Octadecapeptide | Ala—Ala—Cys(186)—Cys—(201) |

F. Audibert, M. Jolivet, L. Chedid, R. Arnon and M. Sela, "Successful Immunization With a Totally Synthetic Diphtheria Vaccine", *Proc. Natl. Acad. Sci. USA,* 79, 5042–5046, 1982.

A peptide containing an amino acid sequence mimicking the antigenic determinant of Streptococcus pyogenes M antigen is as follows:

5 10
Asn—Phe—Ser—Thr—Ala—Asp—Ser—Ala—Lys—Ile—Lys—

15 20
—Thr—Leu—Glu—Ala—Glu—Lys—Ala—Ala—Leu—Ala—

25 30
—Ala—Arg—Lys—Ala—Asp—Leu—Glu—Lys—Ala—

35
—Leu—Glu—Gly—Ala—Met

E. H. Beachy, J. M. Seyer, D. B. Dale, W. A. Simpson and A. H. Kang, "Type-Specific Protective Immunity Evoked By Synthetic Peptide Of Streptococcus Pyogenes M Protein", *Nature,* 292, 457–459, 1981.

Indeed, any amino acid sequence which includes at least the antigenic determinant for a specific antigen can be employed in the present invention.

A sequence of amino acids for the human histocompatibility antigen HLA-B7 which determine the antigenic determinant is postulated as Pro Arg Glu Glu Pro Arg corresponding to amino acids 43–48 of the protein.

A sequence of amino acids for the influenza hemagglutinin antigen (X31 strain) which determine the antigenic determinant postulated as Val Glu Arg Ser Lys Ala corresponding to amino acids 105–110 of the protein.

Two sequences of amino acids postulated for the influenza hemagglutinin antigen (Japanese strain) which determine the H-epitopes are Glu Lys Glu Asn Pro Arg corresponding to amino acids 97–102 and Lys Glu Asn Pro Arg Asp corresponding to amino acids 97–102.

A sequence of amino acids for the influenza hemagglutinin antigen (Victoria A strain) which determine the antigenic determinant is postulated as Asn Asp Asn Ser Asp Lys corresponding to amino acids 188–193.

Two sequences of amino acids postulated for the Fowl Plague virus hemagglutinin antigen which determine the antigenic determinants are as follows: Glu Arg Arg Glu Gly Asn corresponding to amino acids 97–102 and Arg Glu Gly Asn Asp, corresponding to amino acids 98–103.

A sequence of amino acids for the human chlorionic Gonadotropin B subunit antigen which determine the antigenic determinate is postulated as Arg Arg Ser Thr Thr Asp corresponding to amino acids 94–99.

A sequence of amino acids for the Human Beta-2 microglobulin antigen which determines the antigenic determinant is postulated as Pro Thr Glu Lys Asp Glu corresponding to amino acids 73–78.

A sequence of amino acids for the human Myelin basic protein antigen which determines the antigenic determinant is postulated as Gly Arg Asp Ser Arg Ser corresponding to amino acids 159–164.

A sequence of amino acids for the Cholera Toxin B-chain antigen which determines the antigenic determinant is postulated as Glu Ala Lys Val Glu Lys corresponding to amino acids 79–84.

A sequence of amino acids for the E. Coli Heat Labile Toxin which determine the antigenic determinant is postulated as Glu Arg Met Lys Asp Thr corresponding to amino acids 66–71.

A sequence of amino acids for the E. Coli Heat Stabile Toxin provides two identical antigenic determinants whose amino acid sequences are postulated as Asp Ser Ser Lys Glu Lys and Ser Glu Lys Lys Ser Glu, which correspond to amino acids 26–31 and 46–41, respectively.

The streptococcial M protein (strain 24) has two identical antigenic determinants whose amino acid sequences are postulated as Arg Lys Ala Asp Leu Glu and Lys Ala Asp Leu Glu Lys, corresponding to amino acids 58–63 and 59–64, respectively.

The trypanosoma brucei variant surface glycoprotein 117 has an antigen determinant whose amino acid sequence is postulated as Lys Ala Lys Glu Lys Gly corresponding to amino acids 50–55.

In the formation of a peptide derived from natural sources, a protein containing the required amino acid sequence is subjected to selective proteolysis such as by splitting the protein with chemical reagents or using enzymes. Synthetic formation of the peptide requires chemically synthesizing the required chain of amino acids.

Chemical synthesis of peptides is described in the following publications: S. B. H. Kent, *Biomedical Polymers*, eds. Goldberg, E. P. and Nakajima, A. (Academic Press, New York), 213–242,(1980); A. R. Mitchell, S. B. H. Kent, M. Engelhard, and R. B. Merrifield, *J. Org.-Chem.*, 43, 2845–2852, (1978); J. P. Tam, T. -W. Wong, M. Riemen, F. -S. Tjoeng, and R. B. Merrifield, *Tet. Letters*, 4033–4036, (1979); S. Mojsov, A. R. Mitchell, and R. B. Merrifield, *J. Org. Chem.*, 45, 555–560, (1980); J. P. Tam, R. D. DiMarchi and R. B. Merrifield, *Tet. Letters*, 2851–2854, (1981); and S. B. H. Kent, M. Riemen, M. Le Doux and R. B. Merrifield, *Proceedings of the IV International Symposium on Methods of Protein Sequence Analysis*, (Brookhaven Press, Brookhaven, N.Y.), in press, 1981.

*Chemical Synthesis:* In the so-called "Merrifield solid phase procedure" the appropriate sequence of L-amino acids is built up from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure. The peptide-resin is:

(a) washed with methylene chloride;
(b) neutralized by mixing for 10 minutes at room temperature with 5% (v/v) diisopropylethylamine (or other hindered base) in methylene chloride;
(c) washed with methylene chloride;
(d) an amount of amino acid equal to six times the molar amount of the growing peptide chain is activated by combining it with one-half as many moles of a carbodiimide (e.g., dicyclohexylcarbodiimide, or diisopropylcarbodiimide) for ten minutes at 0° C., to form the symmetric anhydride of the amino acid. The amino acid used should be provided originally as the N-alpha-tert.butyloxycarbonyl derivative, with side chains protected with benzyl esters (e.g. aspartic or glutamic acids), benzyl ethers (e.g.,serine, threonine, cysteine or tyrosine), benzyloxycarbonyl groups (e.g., lysine) or other protecting groups commonly used in peptide synthesis;
(e) the activated amino acid is reacted with the peptide-resin for two hours at of the new amino acid to the end of the growing peptide chain;
(f) the peptide-resin is washed with methylene chloride;
(g) the N-alpha-(tert. butyloxycarbonyl) group is removed from the most recently added amino acid by reacting with 30 to 65%, preferably 50% (v/v) trifluoroacetic acid in methylene chloride for 10 to 30 minutes at room temperature;
(h) the peptide-resin is washed with methylene chloride; and
(i) steps (a) through (h) are repeated until the required peptide sequence has been constructed.

The peptide is then removed from the resin and simultaneously the side-chain protecting groups are removed by reaction with anhydrous hydrofluoric acid containing 10% v/v of anisole or other suitable (aromatic) scavenger. Subsequently, the peptide can be purified by gel filtration, ion exchange, high pressure liquid chromatography, or other suitable means.

In some cases, chemical synthesis can be carried out without the solid phase resin, in which case the synthetic reactions are performed entirely in solution. The reactions are similar and well known in the art, and the final product is essentially identical.

Isolation from natural sources: If sufficient quantities of the whole protein antigen are available, a limited portion of the molecule, bearing the desired sequence of amino acids may be excised by any of the following procedures:

(a) Digestion of the protein by proteolytic enzymes, especially those enzymes whose substrate specificity results in cleavage of the protein at sites immediately adjacent to the desired sequence of amino acids;
(b) Cleavage of the protein by chemical means. Particular bonds between amino acids can be cleaved by reaction with specific reagents. Examples include: bonds involving methionine are cleaved by cyanogen bromide; asparaginyl-glycine bonds are cleaved by hydroxylamine;
(c) A combination of proteolytic and chemical cleavages.

It should also be possible to clone a small portion of the DNA, either from natural sources or prepared by synthetic procedures, or by methods involving a combination thereof, that codes for the desired sequence of amino acids, resulting in the production of the peptide by bacteria, or other cells.

The present invention can be employed as a diagnostic tool to determine the presence of specific antibodies to specific antigens by employing peptides which mimic the natural antigens.

The peptides utilized in the present invention have no more than 60 amino acids in the peptide chain. In a preferred embodiment, the number of amino acids in the peptide chain may range from between about 6 and about 30 amino acids.

The present invention concerns processes for detecting a given antibody in a sample. One such process involves the following:

(1) contacting the sample (serum) with protein A (e.g., Staphylocci bearing protein A or magnetic protein A),
(2) conducting washing,
(3) contacting the resultant washed mass with a peptide-beta-lactamase conjugate,
(4) incubation and
(5) determining the enzyme activity of the resultant mass.

Protein A in the above method can be replaced by a second antibody, e.g., anti-human IGG, anti-human IGM, anti-human IGE or antibodies to immunoglobulins of any animal species.

The incubation steps utilized in carrying out the above procedures can be effected in a known manner, such as by incubating at temperatures of between about 20° C. and about 50° C. for between about 1 hour and about 48 hours. Washings as described above are typically effected using an aqueous solution such as one buffered at a pH of 6–8, preferably at a pH of about 7, employing an isotonic saline solution.

The coupling of the beta-lactamase enzyme and a peptide can be brought about in a known way, for example, by glutaraldehyde - induced polymerization.

EXAMPLES

Examples 1–2 Sera from persons vaccinated with hepatitis B vaccines

Sera generally preselected on the basis of a high level of antibodies to the HBV S-protein (anti-HBs) were obtained from individuals immunized with one of the following hepatitis B vaccines: Merck, Sharp & Dohme Heptavax-B (MSD) (M. R. Hilleman, E. B. Buynak, W. J. McAleer, A. A. McLean, P. J. Provost and A. A. Tytell, "Hepatitis A And Hepatitis B Vaccines", *Viral Hepatitis*, pp. 395–398, Edited by W. Szmuness, H. J. Alter and J. E. Maynard, Philadelphia, Franklin Institute Press, 1982); Pasteur Hevac-B (Pasteur) (P. R. Guesry, P. Adamowicz, P. Jungers, A. -M. Courouce, A. Laplanche, B. Lacour, E. Benhamou, F. Degos and J. Crosnier, "Vaccination Against Hepatitis B in High-Risk Hemodialysis Units: A Double-Blind Study", *Viral Hepatitis*, pp. 493–507, Edited by W. Szmuness, H. J. Alter and J. E. Maynard. Philadelphia, Franklin Institute Press, 1982); and The Central Laboratory of the Netherlands Red Cross Blood Transfusion Service HB-vaccine (CLB) (E. E. Reerink-Brongers, H. W. Reesink, H. G. J. Brummelhuis, B. J. T. Schut, P. J. Dees, P. N. Lelie, A. K. Raap, L. A. Wilson-Desturler, W. G. Vanaken, H. Balner, P. M. C. A. Van Eerd, T. C. Van Schie, L. W. Stitz, B. Van Steenis and T. M. Feltkamp-Vroom, "Preparation And Evaluation Of Heat-Inactivated HBsAg As A Vaccine Against Hepatitis B", *Viral Hepatitis*, pp. 437–450, Edited by W. Szmuness, H. J. Alter and J. E. Maynard, Philadelphia, Franklin Institute Press, 1982).

Additional sera were used in the course of the development of the ELISA test: rabbit antisera to HBV from which antibodies to the S-protein had been removed (Neurath et al., 1976, supra; A. R. Neurath, S. B. H. Kent, N. Strick, P. Taylor and C. E. Stevens, "Hepatitis B Virus Contains Pre-S Gene Encoded Domains", *Nature* (London), 315, 154–156, 1985; rabbit atisera to the synthetic peptides pre-S(120–145) and pre-S(12–32) (A. R. Neurath, S. B. H. Kent, N Strick, "Location And Chemical Synthesis Of A Pre-S Gene Coded Immunodominant Epitope Of Hepatitis B Virus", *Science*, 224, 392–395, 1984; Neurath, Kent, Strick, Taylor and Stevens, 1985, supra) and pooled serum from individuals vaccinated with an experimental vaccine (McAuliffe et al., 1982, supra). The latter serum pool contained sera of individuals positive for antibodies with anti-pre-S specificity as determined by double antibody radioimmunoassays (RIA) (Neurath, Kent, Strick, Taylor and Stevens, 1985, supra).

For comparison, sera from individuals who were infected with HBV or acquired anti-HBs as a result of HBV infection were also tested for anti-pre-S specific antibodies.

Human sera were tested for anti-HBs by RIA (AUSAB test; Abbott Laboratories, Chicago), and the results were expressed in international milliunits (mIU)/ml calculated from a calibration curve relating cpm to serial dilutions of an international anti-HBs standard.

Preparation of Synthetic Peptide-Beta-Lactamase conjugates

Procedures for the conjugation of antibodies with beta-lactamase (R. H. Yolken, S. -B. Wee and M. Van Regenmortel, "The Use Of Beta-Lactamase In Enzyme Immunoassays For Detection Of Microbial Antigens", *Journal of Immunological Methods*, 73, 109–123, 1984; A. R. Neurath, N. Strick, P. Sproul, L. Baker, P. Rubenstein, C. E. Stevens, P. Taylor, R. C. Gallo, J. W. M. Gold, Y. S. Lee and T. Nilsen, "Radioimmunoassay And Enzyme-Linked Immunoassay of Antibodies To The Core Protein(P24) Of Human T-Lymphotropic Virus (HTLV-III)", *Journal of Virological Methods*, 11, 75–86, 1984) were followed. One mg of either synthetic peptide pre-S(120–145) or pre-S(12–32) (A. R. Neurath, S. B. H. Kent, N. Strick, "Location And Chemical Synthesis Of A Pre-S Gene Coded Immunodominant Epitope Of Hepatitis B Virus", *Science*, 224, 392–395, 1984; A. R. Neurath, S. B. H. Kent, N. Strick, P. Taylor and C. E. Stevens, 1985, supra) in 250 μl of 0.1M phosphate pH 6.8 were each mixed with 2 mg of beta-lactamase (type I, Sigma, St. Louis, MO) (250 μl, 8 mg/ml predialyzed against the same buffer). Fifty μl of 0.2% glutaraldehyde were added to the mixture in 5 μl aliquots. After incubation for 2 hours at room temperature, the conjugate was dialyzed at 4° C. against phosphate-buffered saline, pH 7.4, changed 3 times. Ethanolamine (0.05M) was added to the conjugate after the first dialysis buffer change.

ELISA Tests

Ten μl aliquots of serum samples were mixed with 400 μl of 0.14M NaCl, 0.01M Tris, 0.02% $NaN_3$, pH 7.2 (TS) containing 10 mg/ml of bovine serum albumin (TSB). To determine the dilution endpoints of various sera, serial dilutions (400 μl) were made in TSB containing 0.5% (v/v) normal rabbit serum. Twenty μl of magnetic protein A (Biomag M4600, Advanced Magnetics, nnc., Cambridge, MA) were added to the diluted specimens. After 30 minutes at room temperature, the magnetic protein A with immunoglobulins adsorbed from the serum specimens was separated in a magnetic field using the M4700 magnetic separator (Advanced Magnetics). Excess fluids were aspirated from the magnetic particles which were subsequently washed twice with TSB. The synthetic peptide-beta-lactamase conjugate (400 μl; diluted $2.5\times10^4$-fold in TSB) was added to the magnetic particles and the mixtures were incubated 30 minutes each at 37° C. and 20° C. The particles were separated in a magnetic field and washed twice with TS and once with the substrate solution (1 mg/ml of soluble starch, 15 μg/ml of penicillin G, 30 μg/ml of $I_2$ and 0.8 mg/ml KI in 0.14M NaCl, 0.05M phosphate pH 7.2). Finally, 400 μl of the substrate solution were added and 90 minutes later, the optical density (OD at 570 nm) of the samples was read using the MR600 Microplate Reader (Dynatech Laboratories, Alexandria, VA) after transfer into wells of 96-well plates. The specimens were considered positive for antibodies if the corresponding OD was less than ½ of the OD corresponding to normal serum controls. The performance of the tests was monitored daily by including positive controls [1/5,000 and 1/1,000 diluted rabbit antisera to the peptides pre-S(120-145) and pre-S(12-32)], respectively [anti-pre-S(120-145) and anti-pre-S(12-32)].

Example 1 Establishment of conditions for the ELISA test

Double antibody RIA test and ELISA tests using either synthetic peptide-beta-galactosidase (beta-gal) conjugates (A. R. Neurath, S. B. H. Kent and N. Strick, "Location And Chemical Synthesis Of A Pre-S Gene Coded Immunodominant Epitope Of Hepatitis B Virus", *Science,* 224, 392-395; A. R. Neurath, S. B. H. Kent and N. Strick, "Monoclonal Antibodies To Hepatitis Surface Antigen (HBsAg) With Anti-a Specificity Recognize A Synthetic Peptide Analogue (S-135-155) With Unmodified Lysine", *Journal Of Virological Methods,* 9, 341-346, 1984; A. R. Neurath, S. B. H. Kent, N. Strick, P. Taylor and C. E. Stevens, "Hepatitis B Virus Contains Pre-S Gene Encoded Domains", *Nature (London),* 315, 154-156, 1985), has been used to detect antibodies recognizing synthetic peptide analogues of the HBV env proteins. Using the RIA test, anti-pre-S specific antibodies were detected in sera of 7 out of 12 persons immunized with an experimental hepatitis B vaccine (Neurath, Kent, Strick, Taylor and Stevens, 1985, supra; McAuliffe et al., 1982, supra). These antibodies were not detected in recipients of the MSD vaccine lacking pre-S sequences due to the conditions used for vaccine manufacture (Neurath, Kent, Strick, Taylor and Stevens, 1985, supra). When the RIA test was applied to sera from recipients of two other vaccines (Pasteur and CLB), known to contain small amounts of pre-S sequences at least in some lots of vaccine, only marginally positive results were obtained (RIA ratio units between 2.1 and 3.0) with a portion of vaccine recipients. Negative results were obtained with ELISA assays based on beta-gal conjugates or the corresponding fusion protein. Applicants continued their efforts to demonstrate with confidence the presence of anti-pre-S specific antibodies in vaccinated individuals by attempting to develop more sensitive assays.

First an assay was developed differing from the test finally adopted (see above) in two aspects: (1) Staphylococci bearing protein A were used instead of magnetic protein A, and all separations were done by centrifugation rather than by a magnetic field; and (2) diluted serum samples were first incubated with the synthetic peptide-beta-lacatamase conjugates and the immune complexes were subsequently adsorbed on the Staphylococcal particles. Excellent results were obtained with this test applied to anti-HBV, to anti-peptide sera and to a group of sera from recipients of the Pasteur vaccines. However, screening of normal human and chimpanzee sera surprisingly revealed that a high proportion of sera gave false positive results. This unexpected problem was avoided by adsorbing first the immunglobulins from serum specimens to protein A and subsequently adding the peptide-beta-lactamase conjugate to the washed protein-A-immunoglobulin complexes. Replacement of Staphylococci by magnetic protein A further simplified the performance of the assays.

Figure 2:
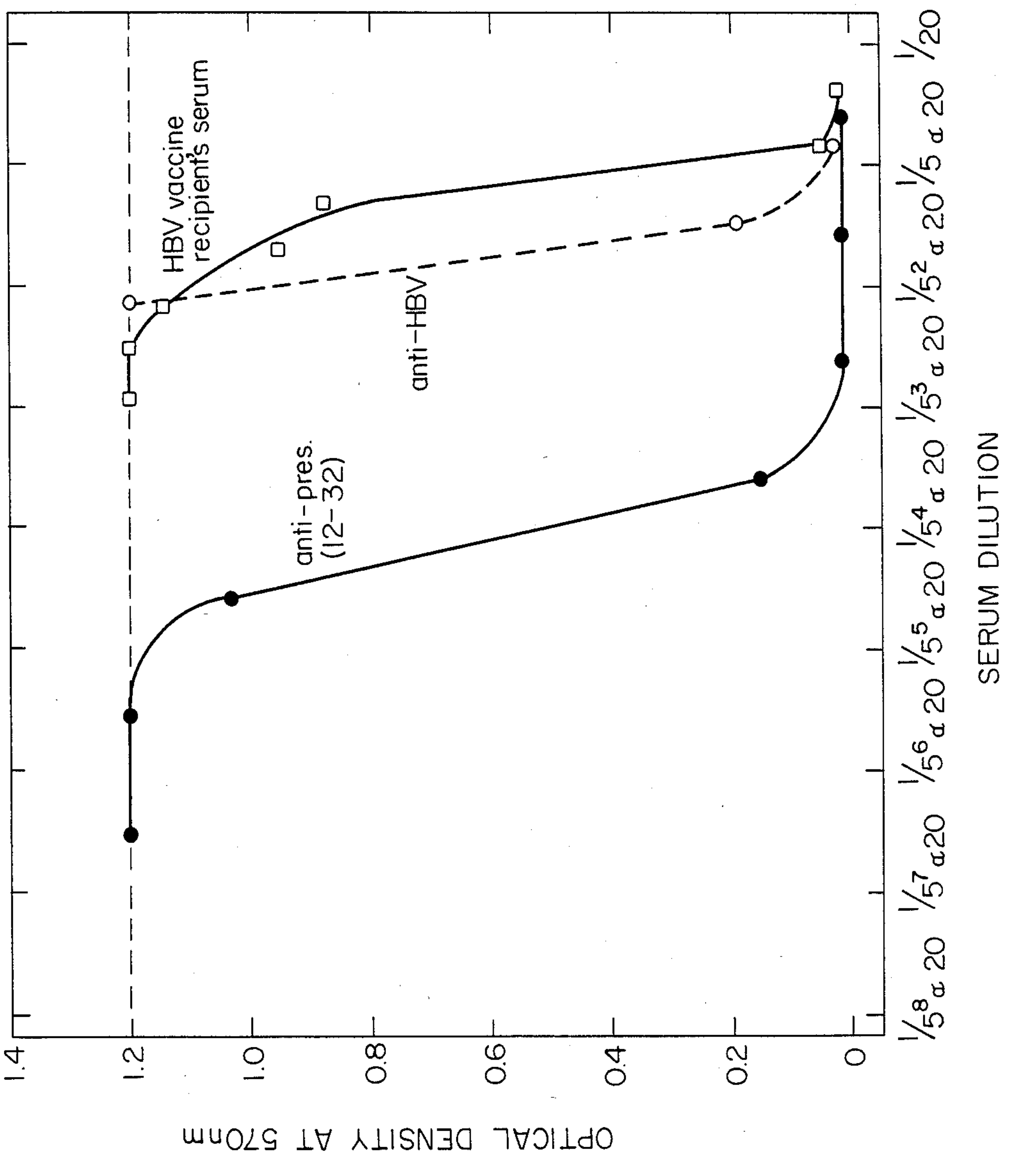
FIG. 2 depicts a graph of optical density (ordinate) vs. serum dilution (abscissa) for results of ELISA tests with serial dilutions of rabbit antisera to HBV and to the synthetic peptide pre-S(12–32); and of a serum from a recipient of a hepatitis B vaccine. The enzyme-labelled antigen was pre-S(12–32)-beta-lactamase.

The dilution endpoints of anti-pre-S(120-145) anti-HBV and pooled sera from hepatitis B vaccine recipients in this assay were approximately $\frac{1}{3}\times10^6$, $\frac{1}{3}\times10^5$ and approximately $1/2.5\times10^4$, respectively, using pre-S(120-145)-beta-lactamase (see FIG. 1). With pre-S(12-32)-beta-lactamase, the respective endpoints were approximately $1/1.25\times10^4$, approximately 1/300 and 1/130 (see FIG. 2). The comparatively lower endpoints for antibodies recognizing pre-S(12-32) in anti-HBV and the human serum pool probably reflects the lower content of the large HBV env protein in HBsAg (HBV) in comparison with the content of middle protein (Heermann et al., 1984, supra, Neurath, Kent, Strick, Taylor and Stevens 1985, supra). The assays were sequence-specific, i.e., anti-pre-S(12-32) did not react with pre-S(120-145)-beta- lactamase and anti-pre-S(120-145) did not react with pre-S(12-32)-beta-lactamase. The assay utilizing pre-S(120-145)-beta-lactamase, because of its higher sensitivity for detection of anti-pre-S specific antibodies, was selected for screening of sera from humans who had been infected with HBV or were immunized with distinct hepatitis B vaccines.

Example 2 Screening of sera for anti-pre-S specific antibodies

Comparative tests with serial dilutions of pooled sera from recipients of a hepatitis B vaccine (McAuliffe et al., 1982, supra) revealed that ELISA tests with pre-S(120-145)-beta-lactamase are approximately 50 to 100 times more sensitive than double antibody RIA tests or ELISA assays with pre-S(120-145)-beta-gal. Sera previously screened by the two latter methods, and found to be negative, were actually positive for anti-pre-S-specific antibodies.

The Pasteur vaccine (except group 2, Table 1) elicited anti-pre-S antibodies in both staff members and patients of hemodialysis units more efficiently than the CLB vaccine, although the latter induced higher levels of anti-S-protein (=anti-HBs) in patients (compare groups 3 and 4 with groups 5 to 7). The antibody responses to either vaccine were higher in personnel than in patients of hemodialysis units. These conclusions were confirmed by determining the anti-pre-S(120-145) dilution endpoints (for comparison, see FIG. 1) of anti-pre-S-positive sera from groups 3,4, and 5, respectively. The corresponding values were approximately 1/5,000, 1/200 and 1/50. Within a single group (compare 4a and 4b) the prevalence of anti-pre-S positive samples was correlated to the level of anti-HBs. In accordance with data reported earlier, the MSD vaccine did not elicit anti-pre-S antibodies. A portion (65%) of homosexual men who acquired anti-HBs as a result of HBV infection had detectable anti-pre-S in their serum. All individuals tested (group 11) who had transient hepatitis B became anti-pre-S-positive in the course of disease in accordance with published data (Neurath, Kent, Strick, Taylor and Stevens, 1985, supra). Interestingly, six of these preselected hemodialysis patients had been vaccinated with the MSD vaccine (all but one patient developed anti-HBs) but were not protected against hepatitis B. (C. E. Stevens, H. J. Alter, P. E. Taylor, E. A. Zang, E. J. Harley and W. Szmuness, "Hepatitis B Vaccine In Patients Receiving Hemodialysis Immunogenicity And Efficiency", *New England Journal of Medicine,* 311, 496-501, 1984).

TABLE 1

Results of screening selected from persons who had been infected with HBV or were vaccinated with distinct hepatitis B vaccines for anti-pre-S-specific antibodies

| | Characterization of population | Source of vaccine* and lot number (if available) | Number of anti-pre-S positive sera per total number of sera tested | Level of anti- (anti-S-protein antibodies) mIU/ml Range | Geometrical Mean |
|---|---|---|---|---|---|
| 1. | Healthy Individuals after receiving 3 doses of vaccine | Pasteur[a] (4) 02 | 10/10 | 2,500-10,500 | 4,460 |
| 2. | Healthy Individuals after receiving 3 doses of vaccine | Pasteur[a] (4) 1005 | 0/12 | 600-12,000 | 7,170 |
| 3. | Hemodialysis Personnel 1 month after 4th dose of vaccine | Pasteur[a] (3) | 15/15 | 53,000-533,000 | 152,000 |
| 4. | Hemodialysis Personnel 1 month after 4th dose of vaccine | Pasteur[a] (3) | 14/20 | 49-15,520 | 646 |
| 4a. | Subdivision of Group 4 | Pasteur[a] (3) | 12/12 | 364-15,250 | 2,150 |
| 4b. | Subdivision of Group 4 | Pasteur[a] (3) | 2/8 | 49-291 | 55 |
| 5. | Hemodialysis Pesonnel 1 month after 4th dose of vaccine | CLB[b] (3) | 11/15 | 50,000-690,000 | 133,800 |
| 6. | Hemodialysis Patients 1 month after 4th dose of vaccine | CLB[c] (3) | 2/20 | 3,200-88,700 | 9,030 |
| 7. | Hemodialysis Patients 1 month after 5th dose of vaccine | CLB[b] (3) | 0/20 | 10,400-119,600 | 40,710 |
| 8. | Healthy Individuals after receiving 3 doeses of vaccine[d] | CLB[b] (5) | 10/25 | 610-7,800 | 1,990 |
| 9. | Hemodialysis Personnel 1 to 5 months after 3rd dose of vaccine | MSD[f] (1) | 0/10 | — | 13,000[e] |
| 10. | Homosexual men who acquired anti-HBs after HBV infection | — (1) | 13/20 | 280-1,020 | 595 |
| 11. | Hemodialysis Patients in the course of transient hepatitis B | — (1) | 10/10[g] | — | — |

*indicates manufacturer of vaccine and, in parenthesis, laboratory from which the sera were obtained, indicated by numbers identical to those given on the title page for the authors' affiliations

[a]vaccine dose = 5 ug

[b]vaccine dose = 3 ug

[c]vaccine dose = 27 ug

[d]different bathces of vaccine were used

[e]The pool of 10 sera was assayed by the AUSAB test.

[f]vaccine dose = 20 ug

[g]Six of these patients had received the MSD vaccine but were not protected.

It will be appreciated that the instant specification and claims are set forth by way of illustration and not limitation, and that various modifications and changes may be made without departure from the spirit and scope of the present invention.

What is claimed is:

1. A reagent for an ELISA determination of antibodies specific for the pre-S region of the hepatitis B virus envelope protein, the reagent comprising a peptide covalently linked to beta-lactamase, wherein said peptide is a synthetic peptide having an amino acid sequence corresponding to a sequence of amino acids in the pre-S region of the hepatitis B virus envelope protein and wherein said peptide mimics an antigenic determinant of said protein.

2. A reagent according to claim 1, wherein the peptide is pre-S(120-145).

3. A reagent according to claim 1, wherein the peptide is pre-S(12-32).

4. A method for detecting a given antibody in a sample, said antibody being specific for the pre-S region of the hepatitis B virus the method comprising:

a. contacting the sample with protein A on a solid support,
b. incubating the resultant mass from step a,
c. washing the resultant mass from step b,
d. contacting the washed mass from step c with a peptide-beta-lactamase conjugate, said peptide of said conjugate mimicing an antigenic determinant of said protein, said peptide being a synthetic peptide having an amino acid sequence corresponding to a sequence of amino acids in the pre-S region of hepatitis B virus envelope protein,
e. incubating the resultant mass from step d,
f. washing the resultant mass from step e, and
g. determining the enzymatic activity of the resultant mass from step f.

5. A method according to claim 4, wherein said peptide is pre-S(120-145).

6. A method according to claim 4, wherein said peptide is pre-S(12-32).

7. A reagent for an ELISA determination of antibodies specific for HTLV III/LAV, the reagent comprising a peptide covalently linked to beta-lactamase, wherein said peptide being a synthetic peptide having an amino acid sequence corresponding to a sequence of amino acids in HTLV III/LAV and wherein said peptide mimics an antigenic determinant of HTLV III/-LAV.

8. A reagent according to claim 7, for the determination of antibodies specific for HTLV III/LAV, wherein said peptide is selected from the group consisting of $NH_2$- T E K L W V T V Y Y G V P V W K E A T T T L F C-COOH, $NH_2$-C R A I R H I P R R I R Q G L E R I L L -COOH, $NH_2$-R A V G I G A L F L G F L G A A G S T M G A R S M-COOH, and $NH_2$-P G G G D M R D N W R S E L Y K Y V V K I E P L G V A P T K A K-COOH.

9. A method for detecting a given antibody in a sample, said antibody being specific for HTLV III/LAV, the method comprising:

a. contacting the sample with protein A on a solid support,
b. incubating the resultant mass from step a,
c. washing the resultant mass from step b,
d. contacting the washed mass from step c with a peptide-beta-lactamase conjugate, said peptide of said conjugate mimicing an antigenic determinant of said protein, said peptide being a synthetic peptide having an amino acid sequence corresponding to a sequence of amino acids in HTLV III/LAV,
e. incubating the resultant mass from step d,
f. washing the resultant mass from step e, and
g. determining the enzymatic activity of the resultant mass from step f.

10. A method according to claim 9, wherein said peptide is selected from the group consisting of $NH_2$-T E K L W V T V Y Y G V P V W K E A T T T L F C-COOH, $NH_2$-C R A I R H I P R R I R Q G L E R I L L-COOH, $NH_2$-R A V G I G A L F L G F L G A A G S T M G A R S M-COOH, and $NH_2$-P G G G D M R D N W R S E L Y K Y K V V K I E P L G V A P T K A K-COOH.

* * * * *

UNITED STATES PATENT AND TRADEMARK OFFICE

CERTIFICATE OF CORRECTION

PATENT NO. : 4,803,156

DATED : Feb. 7, 1989

INVENTOR(S) : Neurath et al.

It is certified that error appears in the above-identified patent and that said Letters Patent is hereby corrected as shown below:

| | |
|---|---|
| Col. 4, line 66 | Delete "b" after "Nos." |
| Col. 5, line 28 | Delete "describe" and substitute --described-- |
| Col. 6, line 18 | Delete "Definitions" |
| Col. 8, line 30 | Correct spelling of --transcript-- |
| Col. 16, line 13 | Insert --room temperature, resulting in addition-- after "at" |
| Col. 17, line 68 | Correct spelling of --antisera-- |
| Col. 18, line 62 | Delete "nnc." and substitute --Inc.-- |

Signed and Sealed this

Eighth Day of May, 1990

*Attest:*

HARRY F. MANBECK, JR.

*Attesting Officer*

*Commissioner of Patents and Trademarks*